United States Patent [19]

Motamedi et al.

[11] Patent Number: 5,824,005
[45] Date of Patent: Oct. 20, 1998

[54] MANEUVERABLE ELECTROPHYSIOLOGY CATHETER FOR PERCUTANEOUS OR INTRAOPERATIVE ABLATION OF CARDIAC ARRHYTHMIAS

[75] Inventors: Massoud Motamedi, League City; David L. Ware, Galveston, both of Tex.

[73] Assignee: Board of Regents, The University of Texas System, Austin, Tex.

[21] Appl. No.: 517,961

[22] Filed: Aug. 22, 1995

[51] Int. Cl.$^6$ .................................................. A61B 17/36
[52] U.S. Cl. .............................. 606/15; 606/33; 600/374; 601/2; 607/122
[58] Field of Search ................................. 606/15, 17, 41, 606/49, 33; 607/89, 101, 122, 126; 128/642; 601/2; 600/374

[56] References Cited

U.S. PATENT DOCUMENTS

| | | | |
|---|---|---|---|
| 4,862,887 | 9/1989 | Weber et al. | 128/303.1 |
| 4,985,028 | 1/1991 | Isner et al. | 606/15 |
| 5,104,393 | 4/1992 | Isner et al. | 606/15 |
| 5,154,501 | 10/1992 | Svenson et al. | 128/419 D |
| 5,169,396 | 12/1992 | Dowlatshahi et al. | 606/15 |
| 5,172,699 | 12/1992 | Svenson et al. | 128/705 |
| 5,188,634 | 2/1993 | Hussein et al. | 606/14 |

(List continued on next page.)

FOREIGN PATENT DOCUMENTS

| | | | |
|---|---|---|---|
| 2560052 | 7/1990 | France . | |
| 1604383 | 8/1985 | U.S.S.R. . | |
| 9210142 | 6/1992 | WIPO | 606/15 |

OTHER PUBLICATIONS

Curtis et al., "Modification of Atrioventricular Conduction Using a Combined Laser–Electrode Catheter," *Pacing Clin. Electrophysiol.*, 17:337–348, Mar. 1994.
AngeLase, Inc. announcement for investigational use only.
Avitall et al., "Physics and Engineering of Transcatheter Cardiac Tissue Ablation", *JACC*, vol. 22(3), 921–32, 1993.
Bashir et al., "Radiofrequency Current Delivery by Way of a Bipolar Tricuspid Annulus–Mitral Annulus Electrode Configuration for Ablation of Posteroseptal Accessory Pathways", *JACC*, vol. 22(2), 350–56, 1993.
Blouin et al., "The Effect of Electrode Design on the Efficiency of Delivery of Radiofrequency Energy to Cardiac Tissue In Vitro", *PACE*, vol. 12, 136–143, Part II, 1989.
Jackman et al., "New Catheter Technique for Recording Left Free–Wall Accessory Atrioventricular Pathway Activation", *Circulation*, vol. 78(3), 598–611, 1988.
Morady et al., "Catheter ablation of ventricular tachycardia with intracardiac shocks: results in 33 patients", *Circulation*, vol. 75(5), 1037–1049, 1987.
Morady et al., "Radiofrequency Catheter Ablation of Ventricular Tachycardia in Patients with Coronary Artery Disease", *Circulation*, vol. 87(2), 363–372 (ed. comment: Dubuc et al., 649–651), 1993.
Svenson et al., "Laser Modification of the Myocardium for the Treatment of Cardiac Arrhythmias: Backround, Current Results, and Future Possibilities", 327–346.
Weber et al., "Percutaneous Nd:YAG Laser Coagulation of Ventricular Myocardium in Dogs Using a Special Electrode Laser Catheter", *PACE*, vol. 12, 899–910, 1989.

*Primary Examiner*—Lee S. Cohen
*Attorney, Agent, or Firm*—Arnold, White & Durkee

[57] ABSTRACT

A catheter capable of both sensing myocardial electrical activity and delivering ablating energy within myocardial tissue is disclosed. The catheter comprises electrodes on the outer sheath and contains a movable fiber optic cable that can be percutaneously advanced beyond the catheter body and into the myocardium for myocardial heating and coagulation, or modification of tissues responsible for cardiac arrhythmias. The fiber optic tip is designed to diffuse ablating energy radially to ablate a larger volume of tissue than is possible with a bare fiber optic tip. In addition, the tip is treated so that energy is not propagated in a forward direction, thus helping to prevent unwanted perforation of the heart tissue.

20 Claims, 5 Drawing Sheets

U.S. PATENT DOCUMENTS

| | | | |
|---|---|---|---|
| 5,222,953 | 6/1993 | Dowlatshahi | 606/15 |
| 5,242,438 | 9/1993 | Saadatmanesh et al. | 606/15 |
| 5,253,312 | 10/1993 | Payne et al. | 385/31 |
| 5,269,777 | 12/1993 | Doiron et al. | 606/7 |
| 5,298,026 | 3/1994 | Chang | 606/15 |
| 5,304,173 | 4/1994 | Kittrell et al. | 606/15 |
| 5,403,311 | 4/1995 | Abele et al. | 606/49 |
| 5,431,649 | 7/1995 | Mulier et al. | 606/41 |
| 5,551,427 | 9/1996 | Altman | 128/642 |

MANEUVERABLE ELECTROPHYSIOLOGY CATHETER FOR PERCUTANEOUS OR INTRAOPERATIVE ABLATION OF CARDIAC ARRHYTHMIAS

BACKGROUND OF THE INVENTION

1. Field of the Invention

The present invention relates generally to the field of medical apparatus and instrumentation and more particularly to the field of non-pharmacologic treatment of cardiac arrhythmias, including percutaneous treatment, with specific application to the ablation or modification of tissues responsible for the arrhythmia.

2. Description of the Related Art

Cardiac arrhythmias arise when the rhythmic electrical signal from the heart's intrinsic pacemakers is not correctly propagated throughout the heart. A particular type of cardiac arrhythmia is a ventricular tachycardia, in which an ectopic focus occurs in the ventricle of the heart resulting in a heartbeat of over 100 beats per minute. This problem often occurs near a site of damaged myocardial tissue caused by an infarction or other injury.

Heating and thus coagulating ("ablating") myocardial tissues responsible for cardiac arrhythmias has been shown to be of great therapeutic value and is frequently done percutaneously ("catheter ablation"). By far the most common method involves delivering radiofrequency energy (RF) via a catheter with a flexible tip equipped with electrodes for sensing ("mapping") the endocardial electrical activation sequence, and for delivering RF energy or laser energy (see Svenson et al., U.S. Pat. No. 5,172,699). The arrhythmias which respond best to this therapy (with a >90% cure rate) are supraventricular. This is due (1) to well-defined mapping criteria highly predictive of cure and (2) to the small volume of tissue which, when ablated, prevents recurrent arrhythmia. Thus only few, or sometimes one, relatively superficial but well targeted, RF-induced lesion(s) may be necessary for success.

This same approach has been far less successful in treating the ventricular arrhythmias typically originating from tissues damaged by myocardial infarction. RF catheter ablation can be recommended only as adjunctive (not "first line") therapy for these arrhythmias. Reasons for this, again, are (1) mapping criteria which are not as clearly correlated with success as in the case of supraventricular arrhythmias and (2) larger tissue volume responsible for the arrhythmia.

An attempt to address the problem of ventricular arrhythmias is described by Isner and Clarke, U.S. Pat. No. 5,104,393, which discloses a catheter for ablation of cardiac tissue. The instrument tip is held in place in the endocardium by a fixation wire, with the ablation tip held on the endocardial wall, and thus, the tip does not directly reach deep intramyocardial tissue where arrhythmias may arise. Other present methods are similarly inadequate for ablating such deep tissue, precluding percutaneous treatment for many patients.

SUMMARY OF THE INVENTION

The present invention addresses the problems described above by (1) delivering laser light or other ablating energy intramyocardially, and (2) diffusing the ablating energy over a broad area in the myocardium without causing excess heat on the endocardial surface or in the blood pool. Mapping of the site of the arrhythmia is made possible by electrodes provided on the catheter sheath that may be switchably connected to a physiological recorder. In a particular embodiment, mapping electrodes may be provided on the retractable tip, in order to more precisely define the area of myocardium in which the arrhythmia arises. The catheter is controllably flexible for placing the electrodes in the correct position for contacting and treating the desired area.

The present invention thus provides instruments and methods for percutaneous catheter ablation of larger myocardial lesions than have previously been possible, by the intramyocardial delivery of diffused laser light, or other ablating energy, thus enhancing the potential for cure of ventricular arrhythmias, for example. Patients may therefore not require pharmacological or surgical therapy, reducing the morbidity and expense of therapy.

The invention, in certain aspects, may be described as an apparatus for endocardial insertion comprising a catheter adapted to access the cardiovascular system. An energy transmitting conductor extends along and within the catheter and has a tip which is extensible beyond the distal end of the catheter and also retractable within the catheter. The conductor may be a conductor for electrical current, ultrasound, microwave, an optical wave guide such as a wave guide for coherent light or a conduit for liquid and most preferably comprises an optical fiber.

The tip of the conductor is configured to penetrate cardiac tissue (i.e. through the endocardium and into the myocardial tissue) and to direct energy from and radially and/or axially relative to the conductor when the conductor is extended beyond the distal end of the catheter and into the myocardial tissue. The tip may form a pointed end, in order to more easily penetrate the endocardium, or the tip may form a flat end, a flat elliptical end or other appropriate configuration. Exemplary tips are described in U.S. Pat. No. 5,253,312, or U.S. Pat. No. 5,269,777 incorporated herein by reference. A preferred tip is the diffusing laser tip available from Rare Earth Medical Lasers Inc., Dennis, Mass. The end of the tip may also be coated or coupled with an energy or light reflecting or deflecting material in order to prevent forward propagation of the ablating energy. This feature increases the safety of the present invention by helping to prevent unwanted perforation of cardiac tissue.

The apparatus may also have one or more electrodes positioned near the distal end of the catheter and may preferably have an electrode pair positioned at the distal end of the catheter to be used to accurately map the arrhythmia. Alternatively, the apparatus may even provide one or more electrodes positioned on the retractable tip for interstitial mapping. Additional electrodes may be positioned on a probe that may be advanced from the end of the catheter into the tissue for recording intramyocardial electrical activity. It is understood that the conductor for the mapping electrodes is preferably incorporated into the sheath of the catheter. However, in those embodiments in which a mapping probe is extensible beyond the catheter sheath, a conductor may pass through the lumen of the catheter in addition to the conductor of ablating energy. Apparatus and methods for stimulating, pacing, and mapping arrhythmias are well known in the art, and they are not, in and of themselves, considered to constitute the present invention. The overall apparatus will preferably include a physiological recorder switchably connected to at least one of the electrodes operable to map local cardiac electrical activity and may further comprise an electrical stimulating device switchably connected to at least one of the electrodes operable to pace or otherwise stimulate the heart tissue. The pacing electrodes may be used to induce or to terminate arrhythmias during the procedure. The apparatus may further comprise a stabilizer, or stabilizing device to help prevent unwanted penetration of heart tissue. The stabilizer is exemplified by, but is not limited to, an inflatable, doughnut-shaped balloon that expands radially and may expand distally relative to the catheter. The stabilizer may be positioned on the outer surface of the catheter to stabilize the catheter within a body organ or cavity. Other stabilizers may include, but are not limited to disk or basket shaped extensions which are attached to the catheter's distal tip.

The present invention may also be described as a maneuverable catheter for ablation of cardiac tissue, where the catheter has a retractable tip, and the tip is extendable into the myocardium tissue for lateral diffusion of ablating energy into the intramyocardial tissue. The ablating energy may be provided in the form of laser energy, radiofrequency energy, microwave, ultrasound or a medium such as hot water, and is preferably 400 to 3,000 nm wavelength laser energy.

A certain aspect of the present invention resides in a method of treating cardiac arrhythmia which comprises the steps of positioning the distal end of an apparatus as described above on the endocardium, identifying the tissue involved in the arrhythmia, extending the distal end of the conductor past the distal end of the catheter and into the tissue, and transmitting ablating energy through the conductor into the tissue. In the practice of this method, the conductor may be a waveguide and the ablating energy may be laser energy. The distal end of the waveguide preferably comprises a penetrating tip and means for distributing laser energy into the selected tissue in a desired pattern, which may be a uniform distribution extending radially from the waveguide.

In certain embodiments, the present invention may be described as a method for promoting myocardial revascularization, through a process called angiogenesis. In the preferred method of practicing this embodiment, the tissues are heated to about 40° C. by introducing the catheter tip into the myocardium which has been previously identified as being underperfused with blood (i.e., ischemic). The procedure would be performed in a manner similar to that described for the treatment of arrhythmias, except in most cases it would be performed intraoperatively and involve a larger volume of tissue.

As used herein, "ablate" means to thermally coagulate and/or remove the tissues where arrhythmias originate or through which arrhythmias are sustained, and in a more general sense, ablation means the desiccation of tissue by the application of heat. For example, an ablating energy would be one that would cause the tissue to reach a temperature of at least about 80°–90° C.

DETAILED DESCRIPTION OF THE PREFERRED EMBODIMENTS

In preferred embodiments, the present invention comprises a catheter capable of both sensing myocardial electrical activity and delivering laser light within myocardial tissue. The distal catheter comprises an outer sheath whereon electrodes are positioned and through which a movable fiber optic cable or other energy delivering device can be percutaneously advanced beyond the sheath and into the myocardium for intramyocardial heating and/or photocoagulation, or modification of tissues responsible for cardiac arrhythmias. Additional mapping data may be obtained by inserting electrodes along a probe into the myocardium, prior to exchanging the mapping probe for the ablating tip. The tip used for intramyocardial heating may be further designed to diffuse photons or other energy laterally, thereby heating larger volumes of tissue than is possible with current endocardial treatments. The tip is designed so that it does not allow forward irradiation, and thus prevents full-thickness ablation and perforation. The overall design of the invention is intended for percutaneous treatment of cardiac arrhythmias such as ventricular tachycardias, although the diffusing tip may also be used intraoperatively. Although treatment of ventricular tachycardia is the most preferred embodiment of the invention, treatment of other arrhythmias may be accomplished with few or no modifications of the disclosed apparatus and methods. In addition, the treatment of ischemic heart disease by laser induction of angiogenesis may be accomplished by the apparatus and methods of the present invention.

Figure 1:
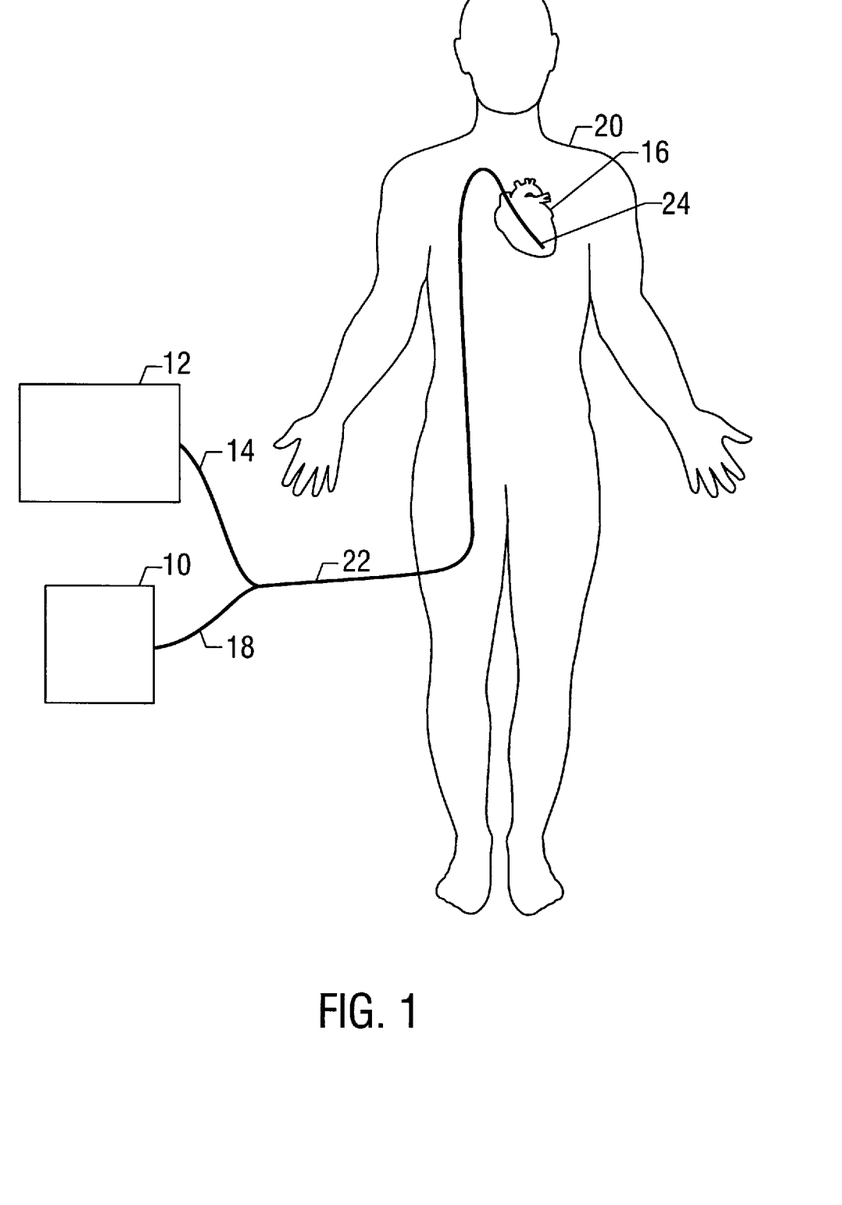
FIG. 1. A schematic of the laboratory arrangement necessary to perform the methods of intramyocardial catheter ablation.

FIG. 1 is a schematic diagram of a preferred embodiment of the present invention in use in a human patient 20. In this embodiment, an external laser source 10, is connected to the distal end 24 of the catheter 22 by a conductor 18 passing through the lumen 44 of the catheter 22 (See also FIG. 2). Also passing through the lumen 44 of the catheter 22 is a conductor 14, connected to a physiological recorder 12, and/or a stimulator 12. Alternatively, the conductor 14 may be incorporated into the sheath 36 of the outer catheter 22. In the embodiment shown in FIG. 1, the catheter 22, is inserted into a femoral artery (or vein), advanced into a chamber of the heart 16, and is placed in contact with the endocardium.

Figure 2:
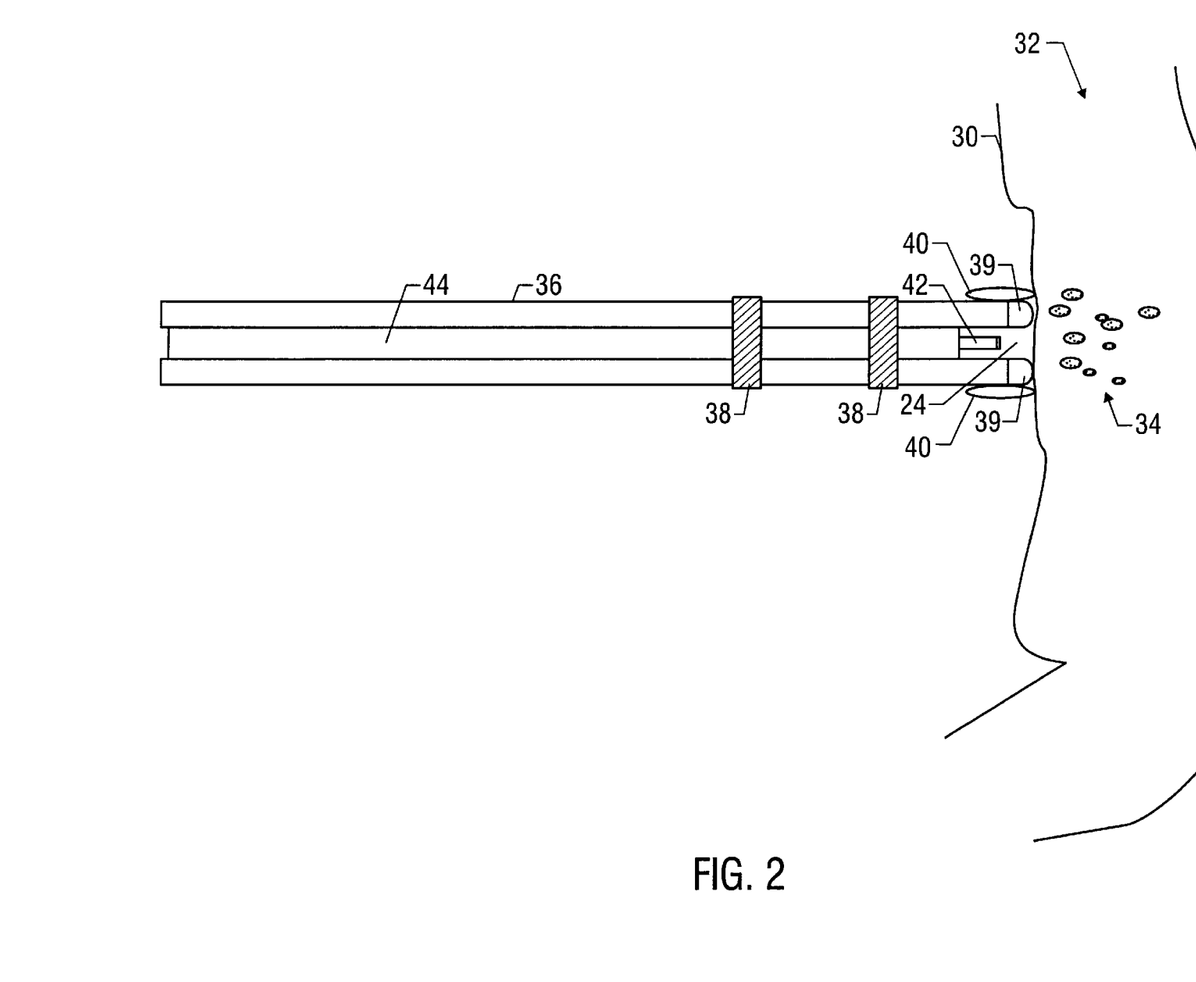
FIG. 2. A schematic drawing of the distal portion of the catheter, with the tip positioned against the ventricular endocardium during mapping, prior to advancement of the fiberoptic diffusion tip and delivery of laser light.

The distal portion of the catheter 22 is shown in FIG. 2. The distal end 24 of the catheter 22 is shown in position against the ventricular endocardium 30 as used during mapping, prior to advancement of the fiberoptic diffusion tip 42 into the interstitial tissue 32 and delivery of laser light into the arrhythmic zone 34. Attached to the catheter sheath 36, is a series of electrodes 38 that may be used for mapping, including one pair 39 positioned at the distal end 24 of the catheter 22. The pair of mapping electrodes 39 positioned at the distal end 24 sense electrical activity, and this information is used to find the arrhythmogenic focus 34 (i.e. the myocardial site giving rise to the arrhythmia). These electrodes 39 at the distal end 24 of the catheter 22 may also be used to pace the heart when pacing techniques are used to assist with mapping. A pair of proximal electrodes 38 positioned along the catheter sheath 36 may then be used to sense endocardial activity during pacing from the distal pair 39. Also shown is an inflatable, circular balloon 40 in the deflated state, ringing the outer surface of the distal end 24 of the catheter 22. The ablating probe tip 42 is retracted entirely within the lumen 44 of the catheter 22, in the unextended position.

Figure 3:
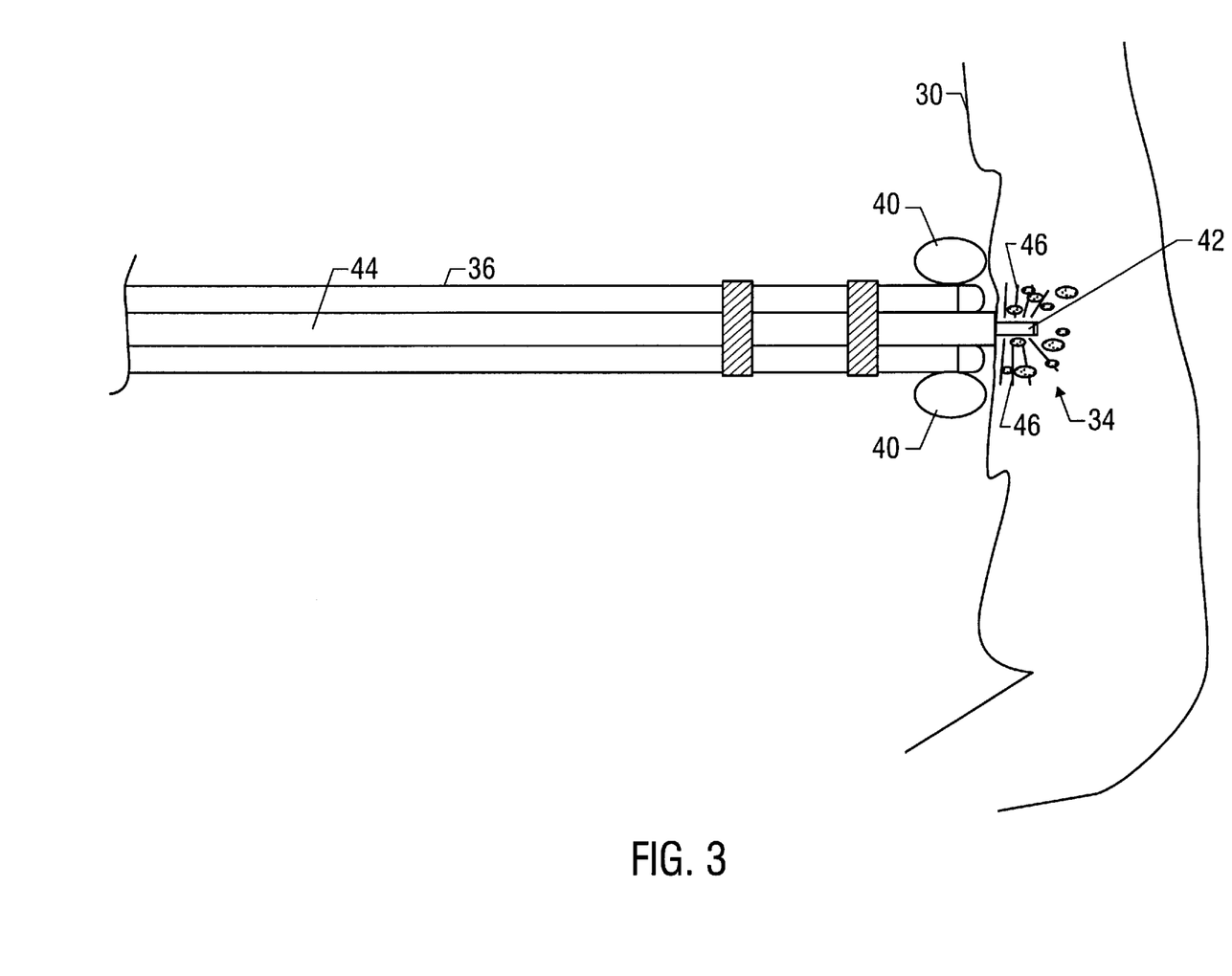
FIG. 3. The catheter of FIG. 2 in the irradiating position, with the penetrating optical fiber tip extended into the myocardium. A circumferential doughnut-shaped balloon has been inflated to help prevent further advancement of the entire catheter system and perforation of the ventricle.
Figure 4A:
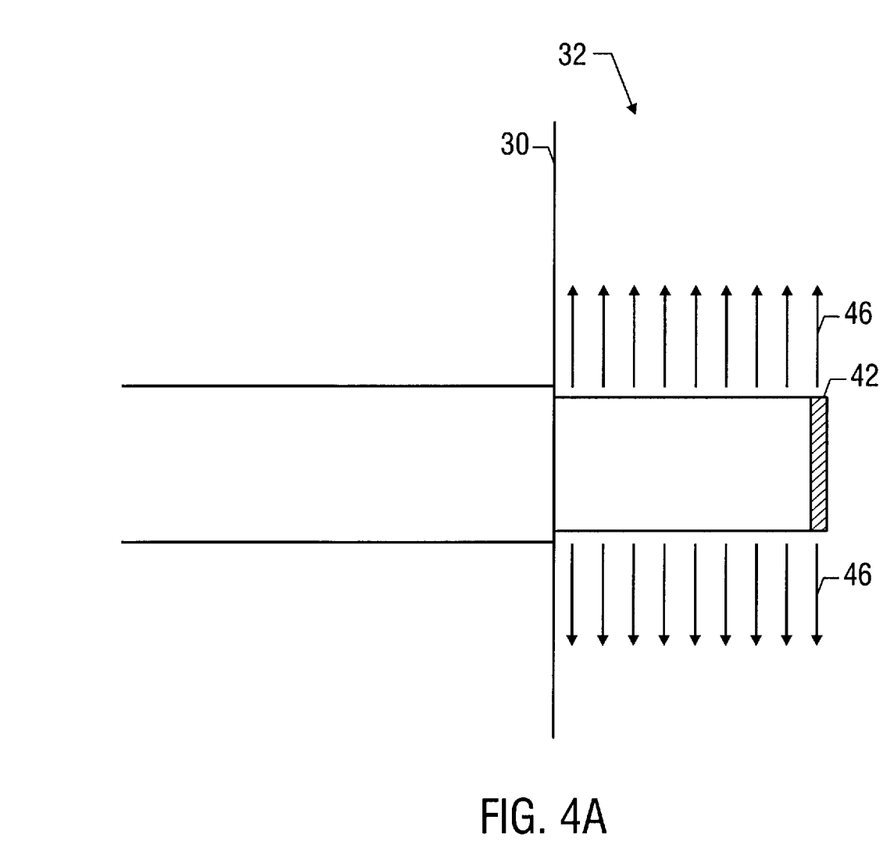
FIG. 4. Schematically depicts the diffusing optical tip and intramyocardial light distribution. The end of the fiber may be coated with or coupled to an optical element to deflect or reflect light so that no light is emitted in the forward direction relative to the tip to prevent perforation and/or damage to the epicardial coronary arteries or pericardium.
Figure 4B:
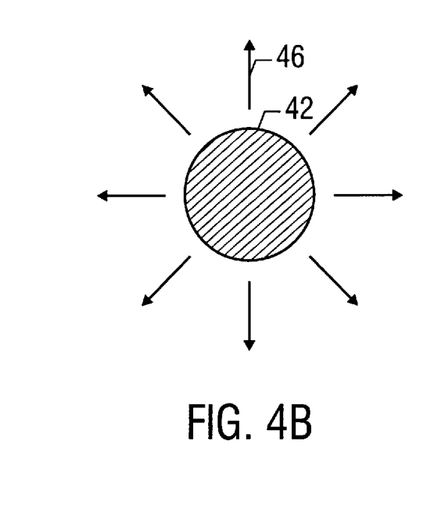

FIG. 3 is a schematic drawing of the catheter 22 in irradiating position. The ablating probe tip 42, is extended beyond the distal end 24 of the catheter 22 and placed intramyocardially for deep tissue coagulation of the arrhythmic zone 34. The stabilizing balloon 40, is shown in the inflated state which inhibits movement of the catheter tip 42 with respect to the heart tissue, and which helps prevent unwanted perforation of the heart tissue by the catheter tip 42. Ablating energy 46 is shown being delivered into the arrhythmic zone 34. FIG. 4 depicts the ablating probe tip 42, in side view and end view. The tip 42 extends from the endocardial wall 30, into the myocardium 32, and radially diffuses the ablating laser energy 46.

Figure 5:
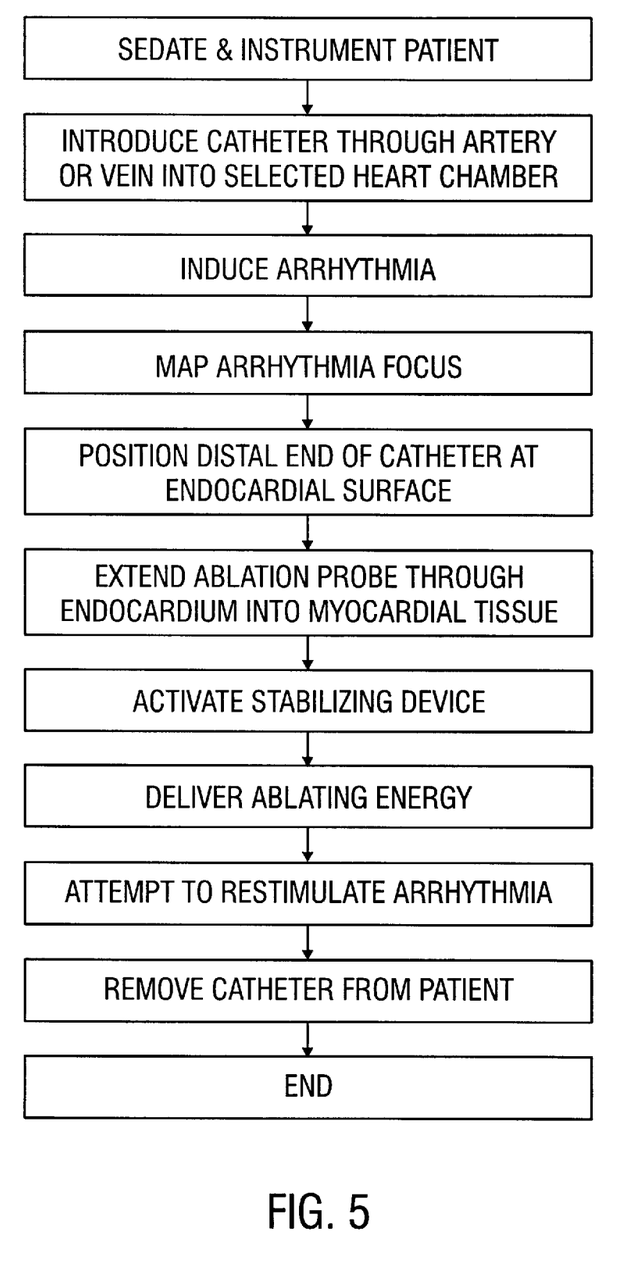
FIG. 5. A flow diagram of a typical method of use of the present invention.

FIG. 5 is a flow diagram of a typical method of use of the present invention, preferably in a human patient. The patient is sedated and instrumented in the standard fashion known to those of skill in the art 72. The catheter system is inserted into a major artery or vein and introduced into the selected heart chamber 52. In a preferred method of treating a ventricular tachycardia the catheter is inserted through the femoral artery. If the arrhythmia to be ablated is not ongoing, it is induced using standard pacing techniques known to those of skill in the art 74. The arrhythmic focus may be mapped 56 by percutaneously flexing the distal end 24 of the catheter 22 so that it contacts multiple endocardial sites, and observing electrical responses transmitted from the mapping electrodes connected to a physiological recorder. The distal end 24 of the catheter 22 is then positioned 58 at the endocardial surface 30 adjacent the arrhythmic zone.

When the distal end 24 of the catheter 22 is in the desired position 58, the tip 42 which may have a pointed end, for example, or may have a flat end, is extended past the catheter sheath 36 a predetermined distance, puncturing the endocardium 30 and extending 60 into the myocardial tissue 32. When the tip 42 is in position, the stabilizing device 40 is activated 62 to prevent perforation. Once in the irradiating position, the entire length of the diffusing component of the tip 42 is embedded below the endocardial surface 30 to avoid irradiating the endocardial surface 30 and the blood pool, thereby helping to prevent endocardial charring and coagulum formation. In certain preferred embodiments, the stabilizing device 40 comprises a balloon which may be inflated or deflated by percutaneously manipulating a handle at the catheter's 22 proximal end.

A predetermined amount of ablating energy 46 is then delivered 64 radially from the tip 42 into the myocardium 32. After delivery of ablation energy 46, an attempt is made to re-stimulate an arrhythmia 66. If needed, further ablating energy 46 is delivered. When no further treatment is necessary or desired, the apparatus is removed from the patient 68 and the procedure is complete 70.

The following examples are included to demonstrate preferred embodiments of the invention. It should be appreciated by those of skill in the art that the techniques disclosed in the examples which follow represent techniques discovered in connection with the invention to function well in the practice of the invention, and thus can be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

EXAMPLE 1

Ablation of Cardiac Tissue in Dogs

For preliminary data, three anesthetized mongrel dogs were used to place 23 intramyocardial lesions from the epicardial surface of the left ventricle (4–12 lesions per dog). The tip of the optical fiber was extended for 8 mm into the myocardium. Three to six Watts of laser energy (805 nm) were administered for 30–120 seconds. The dogs were euthanized and the cardiac tissue was examined. Lesions were from 5.3 to 10.5 mm wide and 7.7 to 12.6 mm deep. No tissue vaporization or marked charring was evident. These studies demonstrate that large but controlled lesions can be made with intramyocardial laser irradiation using the methods and apparatus of the present invention.

EXAMPLE 2

Laser Ablation Treatment of Ventricular Tachycardia in a Human Patient

In a preferred method of practicing the present invention, percutaneous ablation to treat a ventricular tachycardia in a human patient may proceed as follows: The patient, in the electrophysiology laboratory is sedated, instrumented and, with fluoroscopic guidance, the catheter (7 or 8 French) is guided to the heart through a large artery (FIG. 1), preferably through a femoral artery. Programmed stimulation (a standard technique known to those of skill in the art) induces the ventricular or supraventricular tachycardia and the operator "maps" its electrical activation sequence. Mapping is performed during sustained and hemodynamically stable ventricular tachycardia by percutaneously flexing the distal end 24 of the catheter 22 so that it contacts multiple endocardial sites. By sensing the electrical activity at various sites, the arrhythmic focus, or site of origin of the arrhythmia 34 is located.

During the mapping procedure the optical fiber tip 42 is retracted inside the catheter sheath 36 and the distal electrode pair 39 is placed in contact with the endocardium 30 (FIG. 2). The catheter 22 is steered percutaneously by flexing a handle attached to the proximal end of the catheter 22. A number of such handles are commercially available, with a preferred handle being manufactured by Cordis Webster, Inc. 4750 Littlejohn St., Baldwin Park, Calif., 91706. When the area of myocardium to be photocoagulated is located, the fiberoptic tip 42 (200–600 micron diameter) (Rare Earth, Dennis, Mass. or PDT Systems, Goleta, Calif.) is extended 3 to 5 mm from the distal end 24 of the mapping catheter 22, penetrating the endocardium 30 and extending into the target tissue 32 for deep tissue irradiation (FIG. 3). To prevent myocardial perforation, light does not exit from the distal end of the tip 42, but diffuses laterally into a broad area of myocardium (FIG. 4). It is also an aspect of the invention that the energy diffusing tip 42 is completely inserted into the interstitial tissue 32 so that ablating energy is not applied directly to the endocardial surface 30. As a consequence of this procedure the endocardial surface 30 is not charred and is disrupted only by the small puncture site; this is in contrast to the outcome of current treatments using RF and laser energy sources applied to the endocardial surface 30.

Once the tip 42 is in the irradiating position, a small balloon 40 encircling the distal end 24 of the catheter 22 is inflated to stabilize the catheter 22 and help prevent perforation of the heart tissue. Laser energy of 400 to 3,000 nm wavelength is then conducted from the source 10 to the tip 42 and dispersed radially by the tip for 30–120 seconds depending on the wavelength used and the size of lesion necessary to ablate the arrhythmic focus. After the delivery of laser energy, an attempt may be made to re-stimulate the arrhythmia. If the arrhythmia cannot be re-stimulated, the treatment ends and the catheter 22 is removed from the patient. If an arrhythmia is stimulated, then the physician may choose to map the arrhythmia and repeat the procedure.

The present invention may be applied in a similar fashion during arrhythmia surgery to ablate or modify arrhythmogenic myocardium, except the ablation proceeds during direct visualization of the heart. This approach may eliminate certain limitations associated with intraoperative cryoablation.

EXAMPLE 3

Treatment to Induce Angiogenesis

In addition to modifying conduction pathways of the heart for the treatment of cardiac arrhythmias, laser delivery using the device disclosed herein has potential to increase myocardial perfusion in patients with coronary insufficiency. In previous attempts to address this problem, transmyocardial channels 1 mm in diameter have been produced using the high-power (800 Watt) $CO_2$ laser. It has been proposed that these channels convey oxygen rich blood directly to ischemic tissue. Preclinical and clinical results are promising, and the Food and Drug Administration has recently approved a Phase II trial.

However, the theory of revascularization mentioned in the previous paragraph has been challenged by pathological studies showing that laser-induced transmyocardial channels do not remain patent. Alternate theories propose that the improvement seen after this procedure is not due to direct myocardial revascularization, but results from secondary changes which occur during healing, in response to the transient rise in temperature (hyperthermia). There is evidence that hyperthermia provides a transient protective mechanism in the heart. During exposure to laser light, heat shock protein and free radical production may stimulate angiogenesis (the formation of new blood vessels) and improve tissue perfusion. Because the device disclosed herein is capable of intramyocardial heating, it is contemplated to be more effective in promoting angiogenesis than one which irradiates only the hearts's surface.

EXAMPLE 4

Laser-Induced Myocardial Remodeling

Following a myocardial infarction, global left ventricular function may be adversely influenced by the regional changes which occur over time with healing and scar formation. Medical intervention has been shown to favorably alter this "remodeling" process, and reduce the degree of global left ventricular dysfunction which might otherwise occur. It is proposed that the use of the present device to either introduce deep, controlled scarring, or to induce angiogenesis (See Example 3) may also favorably alter the course of post-infarction remodeling.

While the apparatus and methods of this invention have been described in terms of preferred embodiments, it will be apparent to those of skill in the art that variations may be applied to the apparatus and methods described herein without departing from the concept, spirit and scope of the invention. All such variations and modifications apparent to those skilled in the art are deemed to be within the spirit, scope and concept of the invention as defined by the appended claims.

What is claimed is:

1. Apparatus for ablation of cardiac tissue comprising:
   a catheter adapted to access the cardiovascular system, said catheter having a distal end and a proximal end; and
   a conductor extending along and within said catheter for transmitting coherent light energy to said distal end of said catheter, said conductor having a distal end which is extensible beyond the distal end of the catheter and also retractable within the catheter, said distal end of the conductor configured to penetrate cardiac tissue and to direct energy from and radially and axially relative to the conductor when the conductor is extended beyond the distal end of the catheter.

2. The apparatus of claim 1, wherein said catheter has an outer sheath and wherein said apparatus further comprises one or more electrode pairs positioned on said sheath of the catheter proximate said distal end of said catheter.

3. The apparatus of claim 2, wherein one of said electrode pairs is positioned on the distal end of the catheter.

4. The apparatus of claim 2, wherein an electrode pair is positioned on a retractable probe slidably disposed in the catheter and extendable beyond the distal end of said catheter for sensing of intramural electrical activity.

5. The apparatus of claim 2, further comprising a physiological recorder switchably connected to at least one of said electrode pairs operable to map local cardiac electrical activity.

6. The apparatus of claim 2, further comprising an electrical stimulating device switchably connected to at least one of said electrode pairs operable to pace the heart.

7. The apparatus of claim 1, further comprising a stabilizer positioned on an outer surface of the catheter to stabilize the catheter within a body organ.

8. The apparatus of claim 7, wherein said stabilizer comprises an inflatable balloon positioned at the exterior of said distal end of said catheter and operable to expand radially relative to the catheter.

9. The apparatus of claim 1, wherein the conductor comprises an optical wave guide and the energy is laser energy.

10. A maneuverable catheter for ablation of myocardial tissue in a heart, said catheter comprising a retractable tip, a conductor, and a source of radiative energy, wherein said tip is connected through said conductor disposed within said catheter to said source of radiative energy, and wherein said retractable tip is extensible through an endocardial layer and into the myocardium of said heart for lateral diffusion of ablating radiative energy into myocardial tissue when said catheter is inserted intravascularly to position said retractable tip adjacent said endocardial layer of said heart.

11. The maneuverable catheter of claim 10, wherein said ablating radiative energy is selected from the group consisting of laser, microwave and ultrasound.

12. The maneuverable catheter of claim 11, wherein said ablating radiative energy is from 400 to 3,000 nm wavelength laser.

13. A method of treating cardiac arrhythmia comprising the steps of:
    (a) positioning the distal end of the apparatus of claim 1 proximate the endocardium;
    (b) identifying the tissue involved in the arrhythmia;

(c) extending the distal end of the conductor into the tissue; and (d) transmitting ablating energy through the conductor into the tissue.

14. The method of claim 13, wherein the conductor comprises a wave guide and the ablating energy comprises laser energy.

15. A method for myocardial ablation for treatment of cardiac arrhythmias, comprising:

providing a catheter comprising mapping electrodes, stimulating electrodes, and a stabilizer, the catheter being insertable into the heart of a patient and a distal end of the catheter being maneuverable from external to the patient;

providing an optical fiber slidably disposed within the catheter, a distal end of the optical fiber comprising an ablation probe that is extensible beyond the distal end of the catheter and adapted for penetrating myocardial and endocardial tissue, the ablation probe being diffusive so as to deliver laser energy substantially radially into the tissue in which the probe is positioned;

providing electronic stimulating and mapping instruments coupled to the mapping electrodes and to the stimulating electrodes, and providing a laser energy source coupled to the optical fiber;

introducing the catheter into the body of a patient and guiding the catheter into the heart of the patient;

stimulating the heart into an arrhythmic condition using said stimulating electrodes;

mapping electrical signals produced by the heart and locating an arrhythmic site for ablation;

placing the distal end of the catheter proximate the arrhythmic site;

activating the stabilizer;

advancing the optical fiber through the catheter, thus penetrating the ablation probe through the endocardium and into myocardial tissue at the arrhythmic site;

ablating tissue at the arrhythmic site by introducing a desired amount of laser energy into the optical fiber, conducting the laser energy through the optical fiber to the ablation probe, and directing sufficient laser energy into the myocardial tissue at the arrhythmic site to ablate the tissue;

deactivating the stabilizer and removing the catheter and optical fiber from the body of the patient.

16. The method of claim 15 wherein said mapping electrodes are positioned on an electrode probe slideably disposed within the catheter that is extensible beyond the distal end of the catheter and designed to penetrate myocardial tissue.

17. The method of claim 16, further comprising attempting to stimulate the heart into an arrhythmic condition using said stimulating electrodes after the ablating step and before removing the catheter from the body.

18. A method for myocardial ablation for treatment of cardiac arrhythmias in a patient, comprising:

providing a catheter having a distal end and comprising mapping electrodes, stimulating electrodes and a stabilizer, the catheter being insertable into a heart of a patient and said distal end of the catheter being maneuverable from external to the patient;

providing an energy conductor having a distal end and slidably disposed within the catheter, said distal end of the energy conductor comprising an ablation probe that is extensible beyond the distal end of the catheter and adapted for penetrating endocardial and myocardial tissue;

providing electronic stimulating and mapping instruments coupled to the mapping electrodes and to the stimulating electrodes, and providing an ablating energy source coupled to the energy conductor;

introducing the catheter into the body of a patient and guiding the distal end of the catheter into the heart of the patient;

stimulating the heart into an arrhythmic condition using said stimulating electrodes;

mapping electrical signals produced by the heart and locating an arrhythmic site for ablation;

placing the distal end of the catheter proximate the arrhythmic site;

advancing the energy conductor through the catheter, thus penetrating the ablation probe through the endocardium and into the myocardium at the arrhythmic site;

ablating tissue at the arrhythmic site by introducing a desired amount of energy into the energy conductor, conducting the energy through the energy conductor to the ablation probe, and directing sufficient energy into the myocardium at the arrhythmic site to ablate the tissue; and removing the catheter and optical fiber from the body of the patient.

19. The method of claim 18, further comprising attempting to stimulate the heart into an arrhythmic condition using said stimulating electrodes after the ablating step and before removing the catheter from the body.

20. The method of claim 18, wherein the energy source is a laser source, and the energy conductor comprises an optical fiber.

* * * * *